(12) United States Patent
Polley et al.

(10) Patent No.: US 9,801,570 B2
(45) Date of Patent: Oct. 31, 2017

(54) AUDITORY STIMULUS FOR AUDITORY REHABILITATION

(75) Inventors: Daniel B. Polley, Jamaica Plain, MA (US); Kenneth E. Hancock, Milton, MA (US)

(73) Assignee: Massachusetts Eye & Ear Infirmary, Boston, MA (US)

( * ) Notice: Subject to any disclaimer, the term of this patent is extended or adjusted under 35 U.S.C. 154(b) by 544 days.

(21) Appl. No.: 14/128,137

(22) PCT Filed: Jun. 22, 2012

(86) PCT No.: PCT/US2012/043707
§ 371 (c)(1),
(2), (4) Date: May 12, 2014

(87) PCT Pub. No.: WO2012/177976
PCT Pub. Date: Dec. 27, 2012

(65) Prior Publication Data
US 2014/0257131 A1 Sep. 11, 2014

Related U.S. Application Data

(60) Provisional application No. 61/499,871, filed on Jun. 22, 2011.

(51) Int. Cl.
*A61B 5/00* (2006.01)
*A61B 5/12* (2006.01)
(Continued)

(52) U.S. Cl.
CPC .............. *A61B 5/125* (2013.01); *A61B 5/123* (2013.01); *A61B 5/744* (2013.01); *A61M 21/00* (2013.01);
(Continued)

(58) Field of Classification Search
CPC ............ A61B 5/121; A61B 5/12; H04R 25/70
(Continued)

(56) References Cited

U.S. PATENT DOCUMENTS 4,158,920 A 6/1979 Walker
5,549,118 A 8/1996 John
(Continued)

OTHER PUBLICATIONS

International Search Report and Written Opinion issued in PCT/US2012/043707 on Dec. 17, 2012 (9 pages).

*Primary Examiner* — Daniel Cerioni
(74) *Attorney, Agent, or Firm* — Fish & Richardson P.C.

(57) ABSTRACT

Generally, a method performed by one or more processing devices includes generating a graphical user interface that when rendered on a display of the one or more processing devices renders a visual representation of an environment and a visual representation of an object in the environment; retrieving an auditory stimulus with one or more auditory attributes indicative of a location of a virtual target in the environment; receiving information specifying movement of the object in the environment; determining, based on the movement of the object, a proximity of the object to the virtual target; adjusting, based on the proximity, one or more values of the one or more auditory attributes of the auditory stimulus; and causing the one or more processing devices to play the auditory stimulus using the adjusted one or more values.

20 Claims, 5 Drawing Sheets

(51) Int. Cl.
*A61M 21/00* (2006.01)
*G06F 19/00* (2011.01)
*G09B 5/06* (2006.01)
*G09B 19/00* (2006.01)

(52) U.S. Cl.
CPC ...... *G06F 19/3406* (2013.01); *G06F 19/3437* (2013.01); *G09B 5/067* (2013.01); *G09B 19/00* (2013.01); *A61B 5/4836* (2013.01); *A61M 2021/005* (2013.01); *A61M 2021/0027* (2013.01); *A61M 2205/3553* (2013.01); *A61M 2205/3561* (2013.01); *A61M 2205/3584* (2013.01); *A61M 2205/3592* (2013.01)

(58) Field of Classification Search
USPC .......................................... 600/559
See application file for complete search history.

(56) References Cited

U.S. PATENT DOCUMENTS

| | | | |
|---|---|---|---|
| 5,889,843 A | 3/1999 | Singer et al. | |
| 6,328,569 B1 * | 12/2001 | Jenkins | G09B 5/04 434/167 |
| 2007/0033613 A1 * | 2/2007 | Ward, III | H04N 5/44543 725/42 |
| 2008/0015462 A1 | 1/2008 | Merfeld | |
| 2009/0106670 A1 * | 4/2009 | Berndt | H04L 12/1822 715/757 |
| 2009/0268919 A1 * | 10/2009 | Arora | H04R 29/001 381/56 |
| 2009/0318826 A1 * | 12/2009 | Green | A61B 5/048 600/545 |
| 2011/0280409 A1 * | 11/2011 | Michael | H04R 5/04 381/60 |
| 2012/0105225 A1 * | 5/2012 | Valtonen | G01S 19/47 340/539.13 |

* cited by examiner

AUDITORY STIMULUS FOR AUDITORY REHABILITATION

RELATED APPLICATIONS

This application is a 371 U.S. National of PCT/US2012/043707, filed Jun. 22, 2012, which claims priority under 35 U.S.C. §119(e) to provisional U.S. Patent Application 61/499,871, filed on Jun. 22, 2011, the entire contents of each of which are hereby incorporated by reference.

BACKGROUND

A cochlear implant is a surgically implanted electronic device that provides a sense of sound to an individual who is deaf and/or hard of hearing. In an example, an effectiveness of a cochlear implant increases when the recipient of the cochlear implant receives auditory rehabilitation, e.g., relative to the effectiveness of the cochlear implant when the recipient does not receive auditory rehabilitation. Generally, auditory rehabilitation includes programs and/or activities that promote understanding of auditory signals, including, e.g., sounds, music, speech, and so forth.

In an example, auditory rehabilitation includes training an individual to recognize acoustic cues during communication. That is, the acoustic signal may be received, but phonetic and syntactic information must be extracted for the sound to have meaning to an individual. In this example, auditory rehabilitation trains an individual to listen for rhythm, inflection, intonation, and accent in speech communication. Auditory rehabilitation also trains an individual to recognize contextual cues in communication, including, e.g., whether the lips of an individual speaking are pursed or spread apart. Auditory rehabilitation may also train an individual in vowel recognition, as vowels may be the strongest voiced elements of speech.

SUMMARY

In one aspect of the present disclosure, a method performed by one or more processing devices includes generating a graphical user interface that when rendered on a display of the one or more processing devices renders a visual representation of an environment and a visual representation of an object in the environment; retrieving an auditory stimulus with one or more auditory attributes indicative of a location of a virtual target in the environment; receiving information specifying movement of the object in the environment; determining, based on the movement of the object, a proximity of the object to the virtual target; adjusting, based on the proximity, one or more values of the one or more auditory attributes of the auditory stimulus; and causing the one or more processing devices to play the auditory stimulus using the adjusted one or more values.

Implementations of the disclosure may include one or more of the following features. In some implementations, the method also includes detecting, following play of the auditory stimulus, that a location of the object in the environment corresponds to the location of the virtual target in the environment. In other implementations, the actions of receiving, determining, and adjusting are repeated until a location of the object in the environment corresponds to the location of the virtual target in the environment.

In still other implementations, the method includes causing a diagnostic auditory signal to be played on the one or more processing devices; receiving information indicative of a response of a user to the diagnostic auditory signal; determining, at least partly based on the received information, auditory dysfunction in one or more types of auditory perception of the user; generating, based on the determined auditory dysfunction, the one or more auditory attributes; and determining, based on one or more amounts of auditory dysfunction in the one or more types of auditory perception, one or more ranges of values for the one or more auditory attributes.

In some implementations, the one or more ranges of values include one or more ranges of first values, and the method further includes: detecting a decrease in auditory dysfunction of the user; and updating, based on the detected decrease, the first values to second values, with the second values promoting an additional decrease in auditory dysfunction of the user. The method may also include determining, based on the proximity, that the object has moved towards the virtual target; and generating, based on adjusting of the one or more values of the one or more auditory attributes, a notification that the object has moved towards the virtual target.

In other implementations, the method includes determining, based on the proximity, that the object has moved away from the virtual target; and generating, based on adjusting of the one or more values of the one or more auditory attributes, a notification that the object has moved away from the virtual target. In still other implementations, the auditory stimulus promotes auditory rehabilitation in a user of the one or more processing devices by training the user to locate the virtual target in the environment based on a perception of the user of the one or more auditory attributes.

In another aspect of the disclosure, one or more machine-readable media are configured to store instructions that are executable by one or more processing devices to perform operations including generating a graphical user interface that when rendered on a display of the one or more processing devices renders a visual representation of an environment and a visual representation of an object in the environment; retrieving an auditory stimulus with one or more auditory attributes indicative of a location of a virtual target in the environment; receiving information specifying movement of the object in the environment; determining, based on the movement of the object, a proximity of the object to the virtual target; adjusting, based on the proximity, one or more values of the one or more auditory attributes of the auditory stimulus; and causing the one or more processing devices to play the auditory stimulus using the adjusted one or more values. Implementations of this aspect of the present disclosure may include one or more of the foregoing features.

In still another aspect of the disclosure, an electronic system includes one or more processing devices; and one or more machine-readable media configured to store instructions that are executable by the one or more processing devices to perform operations including: generating a graphical user interface that when rendered on a display of the one or more processing devices renders a visual representation of an environment and a visual representation of an object in the environment; retrieving an auditory stimulus with one or more auditory attributes indicative of a location of a virtual target in the environment; receiving information specifying movement of the object in the environment; determining, based on the movement of the object, a proximity of the object to the virtual target; adjusting, based on the proximity, one or more values of the one or more auditory attributes of the auditory stimulus; and causing the one or more processing devices to play the auditory stimulus using the adjusted one or more values. Implementations of this aspect of the present disclosure may include one or more of the foregoing features.

All or part of the foregoing may be implemented as a computer program product including instructions that are stored on one or more non-transitory machine-readable storage media, and that are executable on one or more processing devices. All or part of the foregoing may be implemented as an apparatus, method, or electronic system that may include one or more processing devices and memory to store executable instructions to implement the stated functions.

The details of one or more implementations are set forth in the accompanying drawings and the description below. Other features, objects, and advantages will be apparent from the description and drawings, and from the claims.

DETAILED DESCRIPTION

Figure 1A:
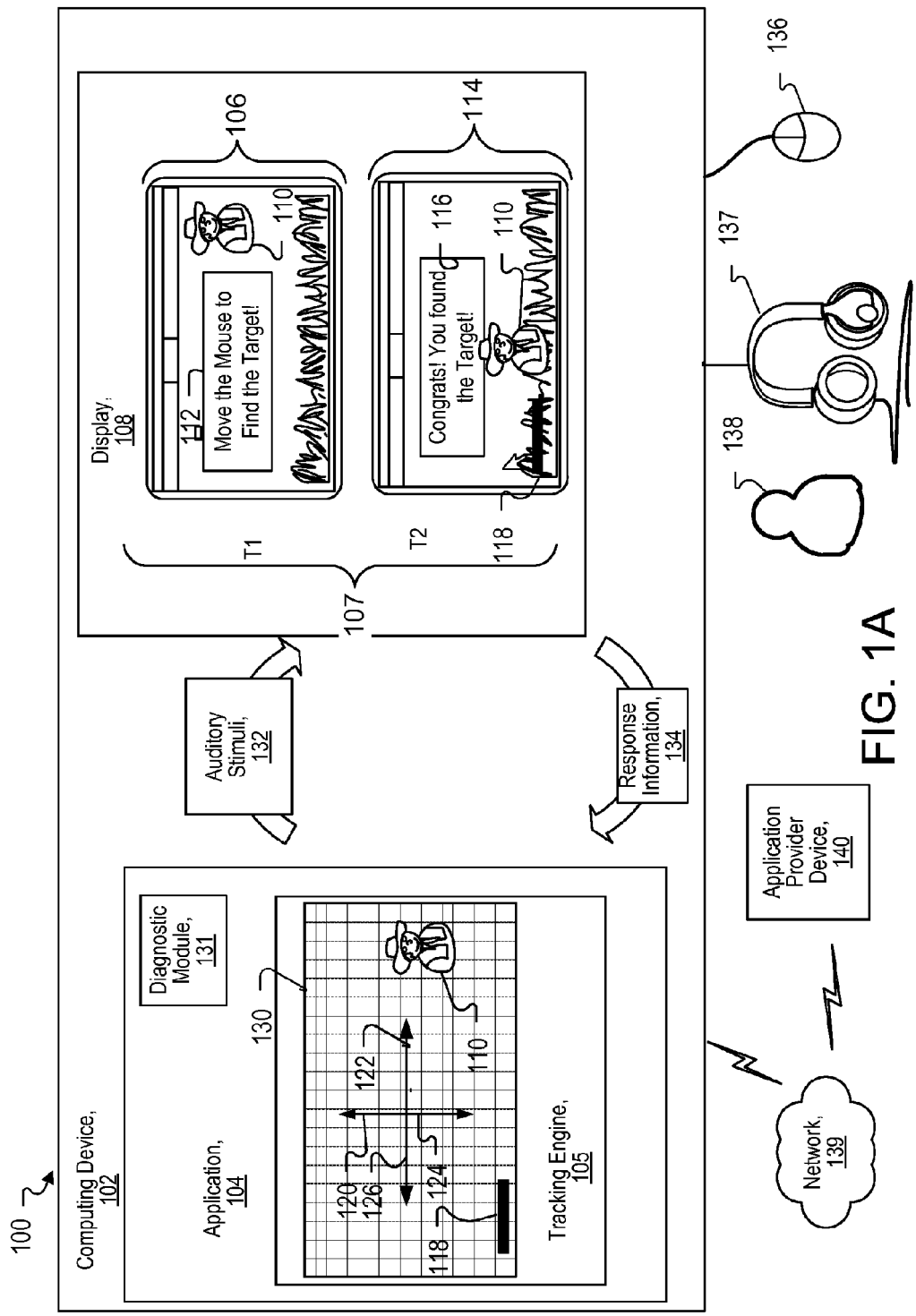
FIG. 1A shows an example system for promotion of auditory rehabilitation.

Described herein is a system and method for promotion of auditory rehabilitation in individuals experiencing auditory dysfunction (e.g., hearing loss, tinnitus, deafness, and so forth) and/or in individuals using cochlear implants. In an example, individuals may experience auditory dysfunction due to maladaptive plasticity in the individual's neural system (e.g., brain). Generally, neural plasticity includes a capacity of the central nervous system to change its structure, chemistry, and physiology according to an individual's specific experiences. The system promotes auditory rehabilitation by promoting adaptive plasticity of brain circuits involved with sound processing in individuals experiencing auditory dysfunction, e.g., relative to the neural plasticity of individuals not receiving auditory rehabilitation.

The system increases the neural plasticity of an individual through implementation of an auditory rehabilitation feedback loop, in which the system provides the individual with auditory stimuli, collects the individual's response to the auditory stimuli, and uses the response to rapidly generate additional auditory stimuli to maximize learning and the underlying expression of brain plasticity in the individual. Generally, an auditory stimulus is includes as acoustic event in an environment that changes electrical activity levels of neurons located in auditory pathways of the brain. By engaging auditory learning in individual experiencing auditory dysfunction, the system allows the individual to more rapidly and accurately recognize auditory stimuli, which improves the hearing of the individual.

In an example, the system efficiently engages therapeutic brain plasticity mechanisms in an individual through implementation of a closed-loop auditory rehabilitation system, in which the auditory stimuli are modified according to the individual's virtual movement patterns in real time. In this example, the individual's decisions about variations in auditory stimuli, as expressed through movement patterns, are nearly instantaneously translated into auditory feedback, which, in turn, can be used to refine subsequent and ongoing auditory-based decisions. Closed-loop approaches increase the efficiency of neurological mechanisms underlying motor and sensory skill learning. By engaging auditory learning in individuals experiencing auditory dysfunction, the system improves the neurological representation of the auditory stimulus, which translates to an improvement in the sensitivity and acuity of hearing in the individual.

In another example, the system includes a portable system that may be used by an individual in a home, an office, a restaurant, a shop, and/or any other location in which the individual may desire to use the portable system. In an example, a portable system may include a system weighing less than ten pounds. Additionally, due to the portable nature of the system, the system includes a portable diagnostic graphical user interface for diagnosis of auditory dysfunction in individuals. The system also includes a portable training graphical user interface that promotes auditory rehabilitation.

In the below examples, techniques are described for treating auditory dysfunction (e.g., hearing loss, tinnitus, deafness, and so forth) in individuals and/or in individuals using cochlear implants. Generally, tinnitus is the perception of noises in the ear which correspond to no acoustic signal in the environment. In an example, the described techniques treat auditory dysfunction by a closed-loop auditory training task, in which the user receives auditory feedback that is linked in real time to sound-guided motor behavior. The closed-loop auditory training task promotes the following events, e.g., (i) the cortical excitatory/inhibitory dysregulation that causes the tinnitus percept is deceased (and/or eliminated) through a brain plasticity-based treatment that does not involve exogenous agents or surgery; (ii) perception of the signal (e.g., acoustic inputs transduced by viable regions of the cochlea) are accentuated, (iii) perception of noise (i.e., phantom sound) is attenuated, and (iv) "top-down" modulation of low-level auditory cortical areas (e.g., by involving working memory and predictive systems) is enhanced.

FIG. 1A shows an example system 100 for promotion of auditory rehabilitation. In the illustrative example of FIG. 1A, system 100 includes computing device 102. Computing device 102 can be a personal digital assistant, a personal computer, a laptop, a server, a cell phone, a mobile computing device, a media-player-type device, a smartphone, a tablet device, a portable computing device, a video game console, and so forth. Computing device 102 is configured for communication with input device 136, including, e.g., a mouse, a video game controller, and so forth. Input device 136 allows user 138 to input into computing device 102 information, including, e.g., text information, movement information (e.g., information indicative of movement of user 138 in the physical world), and so forth.

Computing device 102 is also configured for communication with headphones 137, e.g., for the playing of auditory signals generated by computing device 102. In an example, headphones 137 include a microphone for the input of voice information into computing device 102. Computing device 102 also includes display 108 for the rendering of images and graphical user interfaces, including, e.g., training graphical user interfaces (e.g., graphical user interfaces 106, 114) and diagnostic graphical user interfaces, as described in further detail below.

In a variation of FIG. 1A, computing device 102 may include speakers (not shown) (e.g., rather than headphones 137 or in addition to headphones 137). In this example, computing device 102 may have a wired and/or a wireless connection with the speakers. As described in further detail below, the speakers may also be used in conjunction with diagnostic module 131 to test the heading of user 138.

In the illustrative example of FIG. 1A, user 138 is an individual with auditory dysfunction. In this example, computing device 102 is configured to run an application 104, which promotes auditory rehabilitation in user 138, as described in further detail below. In an example, application 104 includes a video game, an auditory game, a smartphone application, and so forth. System 100 also includes network 139, including, e.g., a wireless network, the Internet, or other types of networks. System 100 also includes application provider device 140, including, e.g., a server or other computing device. In this example, application provider device 140 is configured to store application 104. Computing device 102 accesses network 139 to download application 104 from application provider device 140.

In this example, application 104 promotes auditory rehabilitation in user 138 by mapping properties of an auditory signal onto a visual space, including, e.g., a two-dimensional visual space, a three-dimensional visual space, and forth. Generally, a property of an auditory signal includes a characteristic of an auditory signal that may be detected by user 138. In an example, properties of an auditory signal include spectral characteristics, temporal characteristics, signal-to-noise characteristics, binaural characteristics, and/or any combination thereof (e.g., pitch, tempo, timbre, rhythm, porosity, volume, modulation of a sound envelope, and so forth).

In the illustrative example of FIG. 1A, application 104 generates rehabilitation program 107 as the visual space. In this example, rehabilitation program 107 includes a visual representation of an environment, including, e.g., a virtual world, a gaming world, and so forth. Rehabilitation program 107 includes graphical user interfaces 106, 114 for the display of a visual representation of an object and virtual target 118 to be located by the visual representation of the object. In the illustrative example of FIG. 1A, the object includes avatar 110. A goal of rehabilitation program 107 is for avatar 110, which is controlled by user 138 via input device 136, to locate virtual target 118, which is hidden in graphical user interface 106 when user 138 beings playing rehabilitation program 107.

Application 104 also generates auditory stimulus 132. Generally, auditory stimuli may include one or more auditory attributes. Generally, an auditory attribute includes a property of an auditory signal. In an example, an auditory attribute includes an acoustic cue that provides user 138 with feedback about a proximity of avatar 110 in graphical user interface 106 relative to virtual target 118. In this example, the acoustic cue provides user 138 with the feedback (e.g., real-time feedback) based on the properties of the acoustic cue. Auditory stimulus 132 is mapped onto rehabilitation program 107 by changing the acoustic cues of auditory stimulus 132 during game play, e.g., during real-time game place.

In an example, application 104 may generate dynamic acoustic cues (e.g., in real-time) by modifying the basic properties of an auditory signal, which may include spectral characteristics, temporal characteristics, signal-to-noise characteristics, binaural characteristics, and/or any combination thereof (e.g., pitch, tempo, timbre, rhythm, porosity, volume, modulation of a sound envelope, and so forth). In this example, the pitch of auditory stimulus 132 provides a real-time acoustic cue to user 138 regarding the location of virtual target 118 in graphical user interface 106. As avatar 110 moves towards virtual target 118, the pitch of auditory stimulus 132 adjusts (e.g., increases) in real-time to provide user 138 with an acoustic cue that user 138 has moved avatar 110 towards virtual target 118. Many of the below examples use pitch as the type of acoustic cue. However, the below examples are equally applicable to other types of acoustic cues, which may include acoustic cues based on modifications to spectral characteristics, temporal characteristics, signal-to-noise characteristics, binaural characteristics, and/or any combination thereof (e.g., pitch, tempo, timbre, rhythm, porosity, volume, modulation of a sound envelope, and so forth).

In the illustrative example of FIG. 1A, graphical user interface 106 is rendered on display 108 when user 138 begins playing rehabilitation program 107 at a first point in time, namely, "T1." Graphical user interface 106 includes visual representation 112 of textual information instructing user 138 to move avatar 110 to find virtual target 118. Graphical user interface 114 is rendered on display 108 when avatar 110 finds virtual target 118 at a second point in time subsequent to the first point in time, namely, "T2." In this example, graphical user interface 114 also includes visual representation 116 of textual information congratulating user 138 on finding virtual target 118.

In an example, as user 138 moves avatar 110 via input device 136, computing device 102 generates response information 134, including, e.g., information indicative of a location of avatar 110 in graphical user interface 106 that is rendered on display 108. Using response information 134, application 104 compares a current location of avatar 110 in graphical user interface 106 to virtual target 118 in graphical user interface 106. Based on the comparison, application 104 adjusts in real-time the pitch of auditory stimulus 132 to a level that indicates whether avatar 110 has moved towards or away from virtual target 118. In an example, auditory stimulus 132 may include a range of pitches. As user 138 moves avatar 110 closer to virtual target 118, the pitch of auditory stimulus 132 increases in real-time relative to the pitch of auditory stimulus 132 when user 138 moves avatar 110 away from virtual target 118. As user 138 moves avatar 110 away from virtual target 118, application 104 translates the pitch of auditory stimulus 132, e.g., relative to the pitch of auditory stimulus 132 as user 138 moves avatar 110 towards virtual target 118. Application 104 trains user 138 to locate virtual target 118 by moving avatar 110 in a direction that is consistent with the target pitch of auditory stimulus 132 that has been associated with virtual target 118. By training user 138 to discriminate changes in the pitch of auditory stimulus 132, application 104 induces an adaptive plasticity within the central auditory pathways of user 138, which in turn promotes auditory rehabilitation of user 138.

In an example, application 104 continues the foregoing process of receiving response information 134 and using the received response information 134 to change the pitch of auditory stimulus 132 in real-time, until user 138 locates virtual target 118, e.g., by moving avatar 110 to a location in graphical user interface 114 that corresponds to the location of virtual target 118. Generally, a correspondence includes a similarity or relatedness between two items of information. In this example, the combination of auditory stimulus 132 and response information 134 form the auditory rehabilitation feedback loop between application 104 and user 138 to promote an adaptive neural plasticity of user 138. The auditory rehabilitation feedback loop may be a continuous feedback loop in which application 104 receives response information 134 in real-time and automatically changes the pitch of auditory stimulus 132, based on response information 134.

The effectiveness of auditory rehabilitation is at least partly based on the rate and the efficiency of feedback for auditory-based perceptual decisions. In the illustrative example of FIG. 1A, based on the pitch of auditory stimulus 132, user 138 makes real-time, auditory-based perceptual decisions by deciding in which direction to move avatar 110 in graphical user interface 106. Based on the direction in which user 138 decides to move avatar 110, application 104 changes, in real-time, the pitch of auditory stimulus 132. As previously described, the change in pitch further influences the auditory-based perceptual decisions of user 138, e.g., by indicating whether avatar 110 has moved towards or away from virtual target 118. Because the pitch may be adjusted in real-time, application 104 is configured to increase the rate and the efficiency of feedback on auditory-based perceptual decision in user 138, which promotes accelerated auditory rehabilitation.

In an example, application 104 includes tracking engine 105 to track movement of avatar 110 in graphical user interface 106. In the illustrative example of FIG. 1A, tracking engine 105 includes map 130 to track the movement of avatar 110 in directions 120, 122, 124, 126. Map 130 includes a location of virtual target 118 and a location of avatar 110. As avatar 110 is moved in graphical user interface 106, tracking engine 105 updates map 130 with the location of avatar 110. In an example, tracking engine 105 determines the distance between virtual target 118 and avatar 110 using the coordinates of virtual target 118 in map 130, the coordinates of avatar 110 in map 130, and a distance formula (e.g., the Pythagorean Theorem).

In another example, rehabilitation program 107 operates in a mode where one acoustic dimension is mapped onto a vertical axis and a second dimension is mapped onto a horizontal axis. Virtual target 118 reflects two acoustic properties and user 138 'solves' both acoustic properties in order to identify the location of virtual target 118. In this example, a distance between avatar 110 and virtual target 118 is computed by tracking engine 105 as the separation along each axis.

In an example, as user 138 moves avatar 110 in direction 126 or in direction 124 towards virtual target 118, application 104 increases the pitch of auditory stimulus 132, e.g., relative to a value of the pitch of auditory stimulus 132 when avatar 110 is moved in direction 120 and/or in direction 122 away from virtual target 118. In this example, application 104 determines a value of the pitch of auditory stimulus 132 based on a mapping of the distance between virtual target 118 and avatar 110 to pitch, as shown in the below Table 1:

TABLE 1

| Distance in centimeters ("cm") | Pitch according to the fundamental frequency in Hertz (Hz) |
| --- | --- |
| 4 cm-3.1 cm | 2000 Hz |
| 3 cm-2.1 cm | 2828 Hz |
| 2 cm-1.1 cm | 4000 Hz |
| 1 cm-.1 cm | 5657 Hz |
| 0 cm | 8000 Hz |

As illustrated in the above Table 1, application 104 generates a mapping of pitches for auditory stimulus 132 to a range of distances. In this example, the distance between virtual target 118 and avatar 110 may range from 4 cm-0 cm. As the distance decreases from 4 cm to 0 cm, the pitch of auditory stimulus 132 increases from 2000 Hz to 8000 Hz. In this example, when the location of avatar 110 matches the location of virtual target 118, the distance between virtual target 118 and avatar 110 is about 0 cm and the pitch is 8000 Hz, which is higher than the other pitches included in the mapping of Table 1.

In another example, application 104 dynamically determines the pitch of auditory stimulus 132 using a heuristic algorithm that calculates pitch as a function of one or more parameters, as illustrated in the below Table 2.

TABLE 2

| Pitch (Hz) = 8000 − (distance × 4) |
| --- |

As illustrated in the above Table 2, the heuristic algorithm executed by application 104 uses values of one or more parameters in calculating pitch. In this example, the pitch of auditory stimulus 132 is based on a value for a parameter ("distance parameter") indicative of the distance between virtual target 118 and avatar 110. Application 104 calculates a pitch by multiplying the value of the distance parameter by a value of four and subtracting this resultant value from a value of 8000.

Still referring to the illustrative example of FIG. 1A, user 138 begins playing rehabilitation program 107 at time T1. In this example, tracking engine 105 uses map 130 to calculate the distance between avatar 110 in graphical user interface 106 and virtual target 118. Using the calculated distance, application 104 determines a pitch for auditory stimulus 132, e.g., based on a mapping (e.g., the mapping of Table 1) and/or based on a heuristic algorithm (e.g., the heuristic algorithm of Table 2). In this example, through headphones 137, user 138 hears auditory stimulus 132 at the determined pitch.

In a variation of FIG. 1A, application provider device 140 is configured to store application 104. In this example, computing device 102 accesses over network 139 application 104 from application provider device 140, e.g., rather than downloading application 104 onto computing device 102. In this example, application 104 is deployed over the Internet, via network 139, and is accessible by computing device 102 from application provider device 140.

In another example, application 104 also includes diagnostic module 131 that is configured to diagnose the degree and form of auditory dysfunction in user 138 and to generate rehabilitation program 107 that is specific to user 138 based on the degree and form of auditory dysfunction. In this example, diagnostic module 131 measures an amount of auditory dysfunction in user 138 by analyzing an ability of user 138 to detect changes in various properties of an auditory signal generated by diagnostic module 131 (e.g., a "diagnostic auditory signal").

As previously described, application 104 adjusts values of an acoustic cue (e.g., increasing and/or decreasing pitch) based on a proximity of avatar 110 to virtual target 118. In an example, an acoustic cue is associated with a range of values that may be used for the acoustic cue. In this example, diagnostic module 131 is configured to determine the range of values for an acoustic cue. Diagnostic module 131 determines the magnitude of values and the span of values in the range for an acoustic cue based on the amount of auditory dysfunction exhibited by user 138.

For example, when user 138 exhibits a large amount of auditory dysfunction for a particular type of perception, diagnostic module 131 may generate an acoustic cue with a larger span of values and a larger magnitude of values to promote an ability of user 138 to perceive auditory properties associated with the particular type of perception. In another example, when user 138 exhibits a small amount of auditory dysfunction for another type of perception, diagnostic module 131 may generate an acoustic cue with a smaller span of values and a smaller magnitude of values to increase an ability of user 138 to perceive auditory properties associated with the other type of perception. As diagnostic module 131 detects an improvement in hearing of user 138 (e.g., a decrease in auditory dysfunction), diagnostic module 131 may be configured to dynamically change the magnitude and/or the span of the values included in the ranges for the acoustic cues. To do so, diagnostic module 131 may also receive response information 134. Diagnostic module 131 may use response information 134 to determine whether user's hearing has improved and to adjust the range of values for the acoustic cues accordingly, e.g., by compressing the range of values to make detection of the acoustic cues more difficult and thus increasingly more challenging for user 138.

Diagnostic module 131 measures auditory dysfunction in numerous types of auditory perception, including, e.g., spectral perception, temporal perception, binaural perception, signal-to-noise perception, and so forth. Generally, spectral perception includes an ability of a user to perceive a pitch of an auditory signal. Temporal perception includes an ability of the user to perceive the rate and depth by which the sound pressure envelope is modulated in time. Binaural perception includes an ability of a user to perceive differences in the relative timing and level of auditory stimuli presented to each ear. Signal-to-noise perception includes an ability of the user to perceive an auditory signal among noise, e.g., detecting a tone among babbling speech and/or background noise. Using the types of auditory perception with diagnosed auditory dysfunction, diagnostic module 131 generates rehabilitation program 107 to train user 138 to better perceive the properties of an auditory signal that are associated with the types of auditory perception in which user 138 exhibits auditory dysfunction.

In an example, diagnostic module 131 is configured to measure the spectral perception of user 138 based on a behavioral test that uses pure-tone thresholds (PTTs) to measure hearing sensitivity. PTTs indicate the softest sound audible to an individual at least 50% of the time. Diagnostic module 131 generates a plot of measured hearing sensitivity on an audiogram, which is a graph displaying intensity as a function of frequency.

In an example, diagnostic module 131 has two training modes. In the first training mode, the target sound is remembered by user 138 and user 138 adjusts the sound being heard until user 138 believes the sound being heard matches the target sound user 138 has recalled from memory, as described above. In the second training mode, the target sound is played into one headphone continuously. User 138 moves avatar 110, which changes the sound in the training ear, until the sounds in the training ear matches the target sound user 138 hears in the other ear. Thus, virtual target 118 is the position where the inputs from each ear are equivalent.

In this example, diagnostic module 131 generates a diagnostic graphical user interface (not shown) that when rendered on display 108 renders a visual representation of instructions for user 138 to follow. The instructions specify that user 138 should perform an action when the user 138 perceives a sound. In this example, the action may include selecting a button on input device 136 and/or speaking a pre-defined word (e.g., "sound!").

Based on the softest sound audible to user 138 at least 50% of the time, diagnostic module 131 generates an "audiogram" indicative of the threshold sensitivity across the hearing range of user 138. In this example, diagnostic module 131 analyzes the audiogram to determine whether user 138 exhibits dysfunction in specific frequency ranges. If diagnostic module 131 determines that user 138 exhibits auditory dysfunction in particular frequency ranges, diagnostic module 131 configures rehabilitation program 107 to train user 138 to discriminate pitch changes within the least sensitive frequency ranges previously identified by diagnostic module 131.

In another example, diagnostic module 131 is configured to measure the temporal perception of user 138. In this example, diagnostic module 131 instructs user 138 to perform an action when user 138 detects a change in rate of an auditory signal generated by diagnostic module 131. Based on the ability of user 138 to correctly perceive changes in rate of the auditory signal, diagnostic module 131 generates temporal information indicative of a strength of the temporal perception of user 138.

In still another example, diagnostic module 131 measures temporal perception of user 138 based on envelope modulation discrimination limens, in which user 138 is presented a sequence of two sinusoidally amplitude modulated monaural tones with variable modulation rates. In this example, user 138 indicates whether the tones are the same or different using a standard two-alternative forced choice method, as is commonly known in the art. Diagnostic module 131 may generate temporal information indicative of an ability of user 138 to perceive whether the tones are the same or different.

In this example, diagnostic module 131 analyzes the temporal information to determine whether user 138 exhibits auditory dysfunction in temporal perception. If diagnostic module 131 determines that user 138 exhibits auditory dysfunction in temporal perception, diagnostic module 131 configures rehabilitation program 107 to increase the temporal perception of user 138, e.g., by training user 138 to discriminate changes in the depth or rate of envelope modulations near the limits of their discrimination thresholds that were individually determined by diagnostic module 131.

In yet another example, diagnostic module 131 is configured to measure monaural perception of user 138 by determining discrimination and detection thresholds for user 138 in response to sounds delivered independently to each ear. In this example, diagnostic module 131 may only convey auditory stimuli to the right ear and then ask user 138 to detect with the right ear changes in pitch and/or tempo of an auditory signal. Diagnostic module 131 records information indicative of an ability of the user's right ear to correctly perceive changes in pitch and/or tempo of the auditory signal. Diagnostic module 131 may convey stimuli to the left ear only and ask user 138 to detect changes in pitch and/or tempo in the same auditory signal using the left ear. Diagnostic module 131 records information indicative of an ability of the user's left ear to correctly perceive changes in pitch and/or tempo of the auditory signal. Based on the ability of user 138 to correctly perceive the auditory signal with either ear, diagnostic module 131 generates separate profiles the detection and discrimination thresholds for each ear for user 138.

In another example, diagnostic module 131 tests binaural perception of user 138 by varying the temporal properties or amplitude properties of the sound delivered to each ear of user 138. In an example, user 138 is presented with sinusoidal tones embedded in identical background masking noise to each ear. In normal listeners, the ability to detect the presence of the tone amidst the background noise depends upon their ability to perceive differences between the phase of the sinusoidal tones presented to each ear. When the phase of the tones presented to each ear are inverted, sensitivity to the tones is maximized. When the tones are in phase, there is decreased benefit in sensitivity compared to presenting the tone to one ear alone. Accordingly, this technique may determine the ability of user 138 to recognize tones with variable phase differences embedded in noisy backgrounds. In this example, diagnostic module 131 generates binaural information based on the sensitivity of user 138 to interaural phase cues.

In this example, diagnostic module 131 analyzes the interaural phase sensitivity functions to determine whether user 138 exhibits a deficit in their ability to integrate signals presented to each ear simultaneously. If diagnostic module 131 determines that user 138 exhibits auditory dysfunction in binaural perception, diagnostic module 131 configures rehabilitation program 107 to train user 138 to utilize interaural phase differences near threshold values determined in diagnostic module 131.

In still another example, diagnostic module 131 measures signal-to-noise perception of user 138. In this example, diagnostic module 131 plays background noise. Diagnostic module 131 also instructs user 138 to perform an action when user 138 detects an auditory signal (e.g., a tone) in the background noise. Based on the ability of user 138 to correctly perceive the auditory signal amidst the background noise, diagnostic module 131 generates signal-to-noise information indicative of a strength of the signal-to-noise perception of user 138. This information can in-turn be used to generate rehabilitation program 107.

In another example, diagnostic module 131 measures signal-to-noise perception of user 138 based on speech intelligibility, in which user 138 is instructed by diagnostic module 131 to repeat monosyllabic words (e.g., from the CID W-22 word list used in audiology clinics) into a microphone. Diagnostic module 131 presents a word to user 138 at two different signal levels, including, e.g., at 10 dB and 30 dB above the minimal audible threshold defined from the audiogram under two different signal-to-noise conditions (e.g., a condition of no noise, a condition of babbling speech noise with a root mean square ("RMS") amplitude that is 5 dB below the decibel level of spoken words, and so forth). In this example, diagnostic module 131 generates signal-to-noise information by analyzing the ability of user 138 to correctly perceive the presented word at the different signal levels and at the different signal-to-noise conditions.

In this example, diagnostic module 131 analyzes the signal-to-noise information to determine whether user 138 exhibits auditory dysfunction in signal-to-noise perception. If diagnostic module 131 determines that user 138 exhibits auditory dysfunction in signal-to-noise perception, diagnostic module 131 configures rehabilitation program 107 to train user 138 to perceive signal-to-noise ratios at the threshold limit defined by diagnostic module 131.

In an example, following diagnosis of the amount of auditory dysfunction in user 138, diagnostic module 131 generates rehabilitation program 107 to improve the auditory perception of user 138 through the engagement of neural plasticity mechanisms. In this example, diagnostic module 131 generates rehabilitation program 107 by generating instructions specifying the types of acoustic cues to be included in auditory stimulus 132 and the range of values that may be used for the acoustic cues in auditory stimulus 132.

In an example, application 104 generates numerous challenge levels for rehabilitation program 107. Application 104 may change the challenge level of rehabilitation program 107 based on a proficiency of user 138 in locating virtual target 118. In this example, as user 138 becomes more proficient in locating virtual target 118, application 104 increases a difficulty of rehabilitation program 107 by adjusting the challenge level to a more difficult level of play. A level of play becomes more difficult by reducing an amount of time in which user 138 may locate virtual target 118. The level of play may also become more difficult by compressing the range of values for the acoustic cues (e.g., making the cues more similar to one another). The level of play may also become more difficult by making the target area (e.g., virtual target 118) smaller.

In another example, application 104 generates a score indicative of an ability of user 138 to locate virtual target 118 in rehabilitation program 107. In this example, the score is at least partly based on numerous factors, including, e.g., an amount of time required for user 138 to locate virtual target 118, the challenge level of rehabilitation program 107 when user 138 locates virtual target 118, and so forth.

In an example, application provider device 140 is configured to track and to store scores of other users of other rehabilitation programs generated by application provider device 140 and/or by other applications downloaded from application provider device 140. In this example, application 104 may display for user 138 information indicative of the scores of the other users, e.g., to promote competition among user 138 and the other users and/or to incentivize user 138 to beat the scores of the other users.

In still another example, rehabilitation program 107 may be used by user 138 over multiple consecutive training sessions spanning several days to several months. In yet another example, user 138 may spend a variable amount of time using rehabilitation program 107, including, e.g., fifteen minutes per day, thirty minutes per day, sixty minutes per day, and so forth. Application 104 may also be configured to track performance on past sessions of play of rehabilitation program 107 and to adjust the difficulty level of rehabilitation program 107 accordingly at the start of a new training session of rehabilitation program 107.

In an example, application 104 may be configured to display a rehabilitation program (not shown) that uses distributed targets, in which target locations are reflected in the outline of shapes that are traced by user 138. In this example, the rehabilitation program includes a closed-loop auditory tracing task, e.g., which is implemented in real-time by application 104. For example, in user 138, low-level areas of the auditory cortex feature an over-representation of sound frequencies bordering the hearing loss and a disorganized representation of sound frequencies in the deafferented zone of the tonotopic map. In this example, the closed-loop auditory tracing task differentiates the tonotopic representation within the expanded zone and reformats the disorganized region such that the region features an orderly representation of residual hearing frequencies, thereby improving tinnitus and/or decreasing an about of auditory dysfunction (e.g., hearing loss).

Figure 1B:
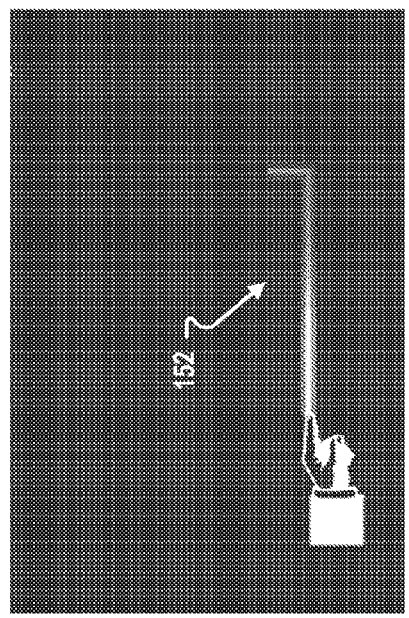
FIGS. 1B-1E show examples of a distributed targets for promotion of auditory rehabilitation.

Through the closed-loop auditory tracing task, users are trained to make fine discrimination of sound frequencies surrounding the hearing loss (i.e., the signal) while suppressing the tinnitus percept (i.e., the noise). That is, the tone frequencies are associated with the level and/or with the type of hearing loss experienced by user 138. Additionally, the noise is indicative of an amount of tinnitus experienced by user 138. Referring to FIG. 1B, user 138 is trained to make a fine discrimination of sound frequencies surrounding the hearing loss, while suppressing the tinnitus percept, by having user 138 trace the outline of invisible polygon 150, e.g., guided only by real time auditory feedback. The sound that user 138 hears at any instant is defined by the properties of the center pixel occupied by a finger of user 138 or a pointer used by user 138, in addition to the ongoing noise, which is generated by diagnostic module 131.

In the example of FIG. 1B, region 151 surrounding polygon 150 is representative of the noise, including, e.g., a spectrally filtered speech babble that masks the tinnitus percept. Polygon 150 is represented by a range of tone frequencies bordering the hearing loss. As described above, the tone frequencies may be selected to improve a type of hearing loss experienced by user 138. In this example, application 104 alerts user 138, when user 138 is tracing at the top of the outline of invisible polygon 150, by rendering a tonal stimulus. Application 104 alerts user 138 to the fact that user 138 is straying further from the outline, as the tone becomes weaker, e.g., leaving only the ongoing noise used to mask the tinnitus percept.

The tones associated with the outline change, in real-time, to include a range of frequencies to differentiate and to reformat the abnormal regions of the brain (i.e., near where the hearing loss occurs). In another example, the change in frequencies along the outline could vary randomly or be made to signal a particular event (e.g., an increase or a decrease in frequency could signal an upcoming shift in the outline contour to the right or to left, respectively).

In the example of FIG. 1B, various portions of polygon 150 are displayed in various colors. In this example, each color is indicative of a particular tone frequency in the above-described range of tone frequencies. As user 138 traces the various portions of polygon 150, which are initially hidden, the various portions of polygon 150 are displayed in display 108 in accordance with the various colors associated with the various portions.

Figure 1C:
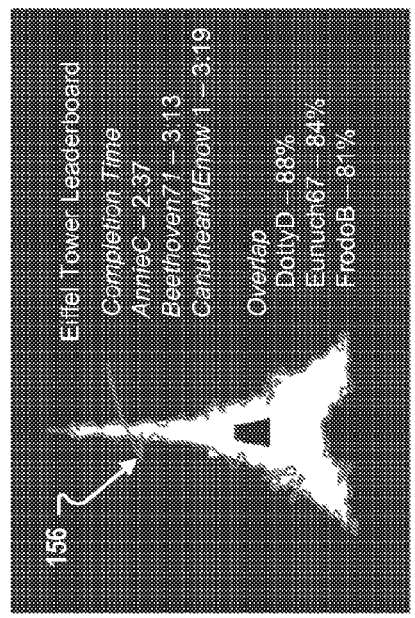

Referring to FIG. 1C, application 104 encourages the involvement of predictive/working memory systems of user 138 by cueing user 138 to the semantic category to which the polygon belongs (e.g., simple shapes, sports equipment, famous monuments) and by leaving fading vapor trail 152 of the outline that user 138 has recently traced, which would provide some information to user 138 about which portion of polygon 150 user 138 should trace next. In this example, fading vapor trail 152 displays portions of polygon that user 138 has correctly traced and identified. In another example, application 104 is configured to briefly flash on display 108 the target shape (e.g., polygon 150) before the trial begins so that user 138 has a higher-order representation of what to trace. In this example, fading vapor trail 152 displays various colors that correspond to the above-described range of tone frequencies for the portions of polygon included in fading vapor trail 152.

Figure 1D:
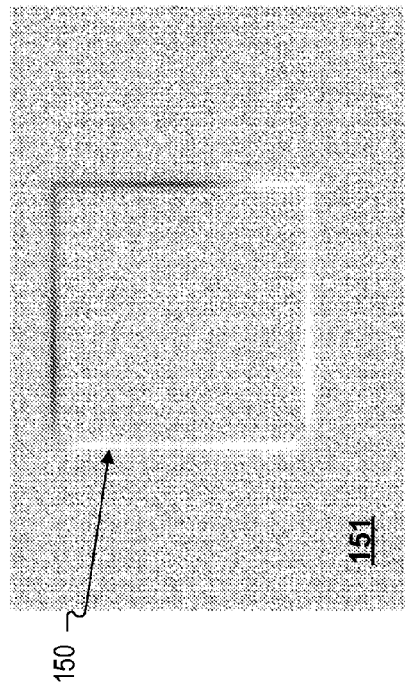

Referring to FIG. 1D, at the end of a trial (e.g., at the completion of the rehabilitation program), user 138 is shown diagram 154, which represents the disparity between the path traced by user 138 and the target shape e.g., polygon 150. In this example, diagram 154 may also display information specifying a completion time in which user 138 identified polygon 150 and an overlap score. Generally, an overlap score includes information indicative of a percentage of overlap between the outline of polygon 150 and the outline that user 138 traced. In an example, where application 104 is implemented as a multi-player game, diagram 154 may also display information showing completion time for other users and overlap scores for the other users.

Figure 1E:
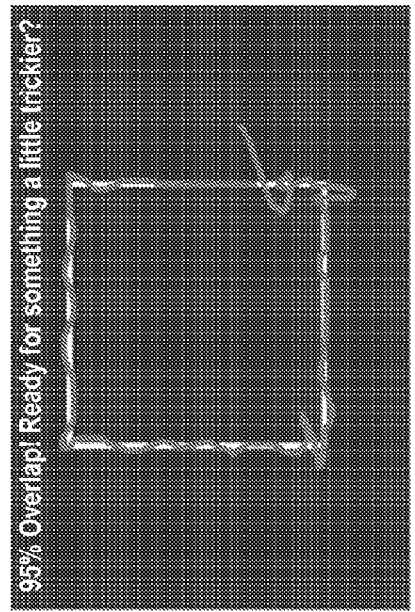

Referring to FIG. 1E, another polygon 156 is presented to user 138. In this example, polygon 156 is associated with increased difficulty of tracing, e.g., relative to the difficulty of tracing polygon 150. Additionally, the tracing of polygon 156 may be made more difficult by adjusting various attributes of application 104, including, e.g., giving user 138 less time to "solve" the problem (e.g. less time to trace polygon 156), increasing the falloff slope such that user 138 gets less warning when user 138 is straying from the outline of polygon 156, making the frequency changes that signal a change in the contour orientation of polygon 156 more subtle, and making the shapes more complicated (e.g., as shown by polygon 156).

Figure 2:
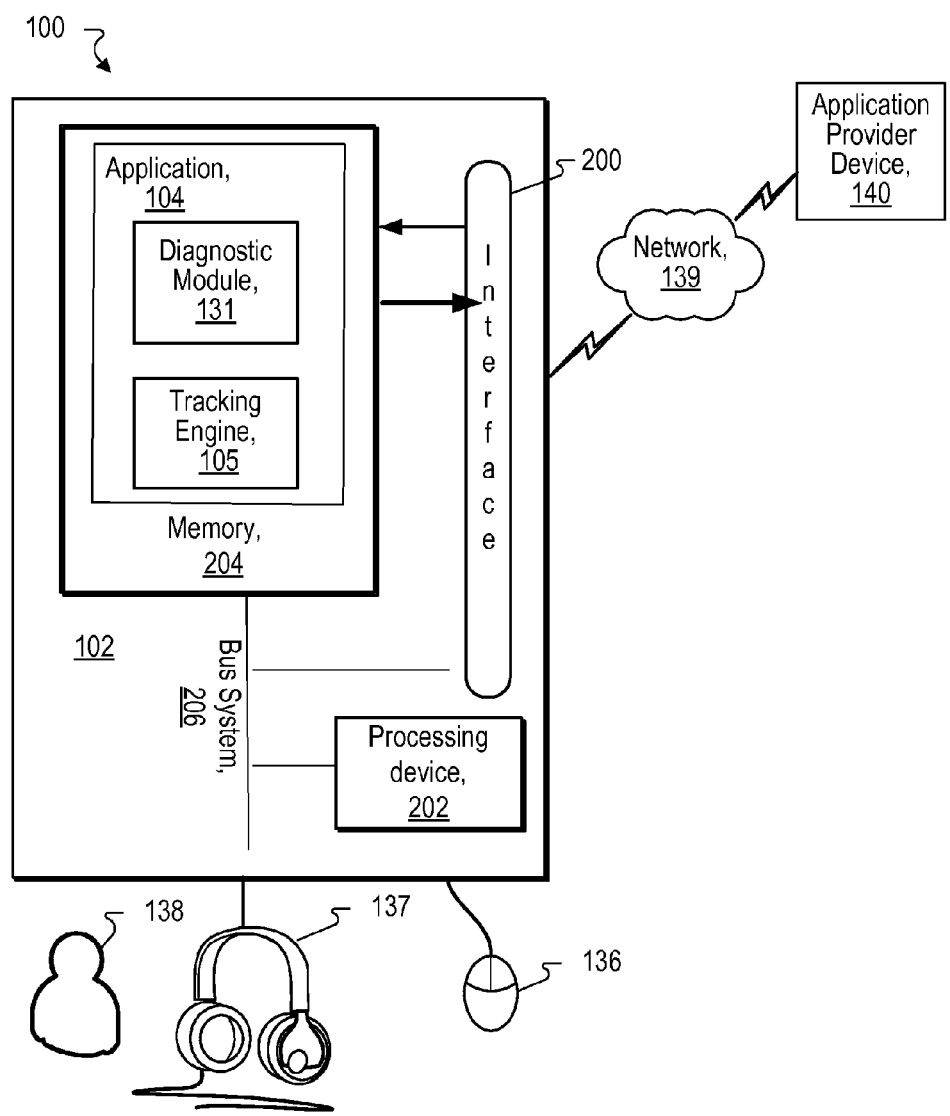
FIG. 2 is a block diagram of the example system for promotion of auditory rehabilitation.

FIG. 2 is a block diagram of system 100 for promotion of auditory rehabilitation. In FIG. 2, references numbers 106-108, 110, 112, 114, 116, 118, 120, 122, 124, 126, 130, 132, 134 are not shown.

In the illustrated example of FIG. 2, computing device 102 can receive information from application provider device 140 via input/output ("I/O") interface 200 over network 139. I/O interface 200 can be any type of interface capable of receiving information over a network, such as an Ethernet interface, a wireless networking interface, a fiber-optic networking interface, a modem, and so forth. Computing device 102 also includes a processing device 202 and memory 204. A bus system 206, including, for example, an information bus and a motherboard, can be used to establish and to control information communication between the components of computing device 102.

Processing device 202 may include one or more microprocessors. Generally, processing device 202 may include any appropriate processor and/or logic that is capable of receiving and storing information, and of communicating over a network (not shown). Memory 204 can include a hard drive and a random access memory storage device, such as a dynamic random access memory, or other types of non-transitory machine-readable storage devices. As shown in FIG. 2, memory 204 stores computer programs that are executable by processing device 202. These computer programs include application 104, tracking engine 105, and diagnostic module 131.

Figure 3:
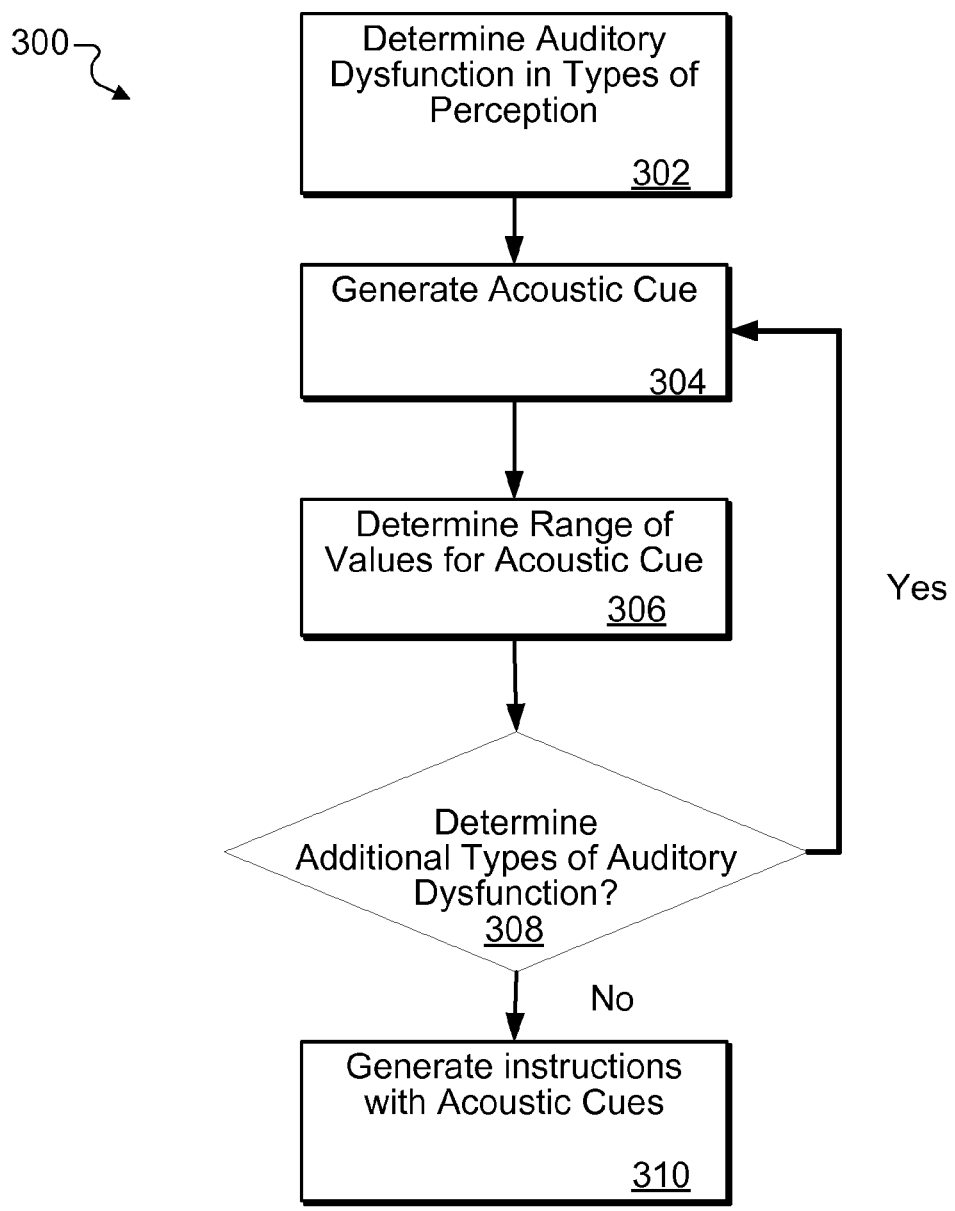
FIG. 3 is a flow diagram of an exemplary process for diagnosing types of auditory dysfunction.

FIG. 3 is a flow diagram of exemplary process 300 for diagnosing types of auditory dysfunction. In operation, diagnostic module 131 determines (302) one or more types of auditory perception in which user 138 exhibits auditory dysfunction. As previously described, user 138 may exhibit auditory dysfunction in spectral perception, temporal perception, binaural perception, signal-to-noise perception, and so forth. Additionally, diagnostic module 131 is configured to diagnose auditory dysfunction using the techniques described herein.

Using the diagnosed types of auditory dysfunction, diagnostic module 131 generates (304) an acoustic cue. As described in further detail with regard to FIG. 4, this acoustic cue is included in auditory stimulus 132 for promotion of auditory rehabilitation in the type of auditory dysfunction. That is, diagnostic module 131 is configured to diagnose types of auditory dysfunction and generate auditory cues based on the diagnosis. Promotion of auditory rehabilitation is performed through rehabilitation program 107, as described in further detail in FIG. 4.

Following generation of an acoustic cue, diagnostic module 131 determines (306) a range of values for the acoustic cue. The range of values may be based on an amount and/or severity of auditory dysfunction identified by diagnostic module 131. In an example, diagnostic module 131 determines that user 138 exhibits a loss of sensitivity to a particular range of frequencies. In this example, for the acoustic cue to promote rehabilitation of sound level perception in user 138, diagnostic module 131 determines the range of values to be 50 db-70 db. In another example, diagnostic module 131 determines that user 138 exhibits a severe amount of auditory dysfunction in pitch discrimination. In this example, for the acoustic cue to promote rehabilitation of pitch perception in user 138, diagnostic module 131 determines the range of values to be 1-2 octaves, thereby increasing the range values when user 138 exhibits severe auditory dysfunction in spectral perception relative to the range of values when user 138 exhibits moderate auditory dysfunction.

In the illustrative example of FIG. 3, diagnostic module 131 determines (308) if there are additional types of auditory dysfunction for which acoustic cues should be generated. That is, an acoustic cue is generated for each type of auditory dysfunction diagnosed in action 302. Accordingly, actions 304, 306, 308 are repeated for each type of auditory dysfunction. If diagnostic module 131 determines that there are additional types of auditory dysfunction for which acoustic cues should be generated, diagnostic module 131 repeats actions 304, 306, 308, until diagnostic module 131 determines that there are no additional types of auditory dysfunction for which acoustic cues should be generated.

When diagnostic module 131 determines that there are no additional types of auditory dysfunction for which acoustic cues should be generated, diagnostic module 131 generates (310) instructions that include the acoustic cues and the range of values for the acoustic cues. In an example, application 104 uses the instructions in generating auditory stimulus 132, e.g., by generating auditory stimulus 132 that blends together the various acoustic cues with values for the acoustic cues that are within the range of values. In a variation of FIG. 3, diagnostic module 131 determines the type of auditory dysfunction, the acoustic cues, and the range of values for the acoustic cues.

Figure 4:
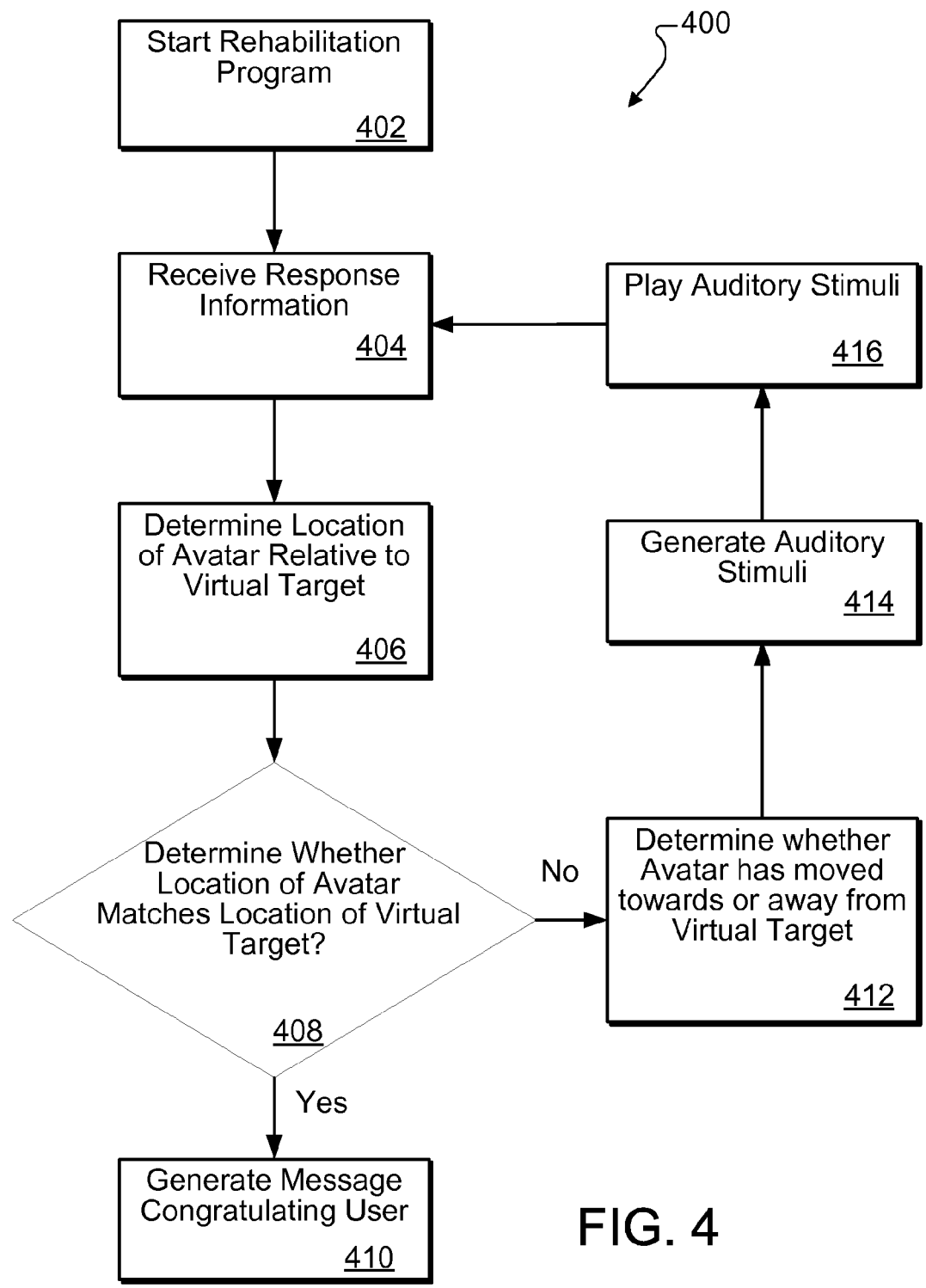
FIG. 4 is a flow diagram of an exemplary process for promotion of auditory rehabilitation.

FIG. 4 is a flow diagram of exemplary process 400 for promotion of auditory rehabilitation. In operation, application 104 starts (402) rehabilitation program 107, e.g., by causing graphical user interface 106 to be displayed on display 108 of computing device 102. As previously described, following display of graphical user interface 106 at time T1, user 138 moves avatar 110 via input device 136 in an effort to locate virtual target 118.

As user 138 moves avatar 110 in graphical user interface 106, computing device 102 regenerates response information 134 that includes information indicative of a location of avatar 110 in graphical user interface 106. Computing device 102 sends response information 134 to application 104. Tracking engine 105 receives (404) response information 134. Using response information 134, tracking engine 105 updates (not shown) the location of avatar 110 on map 130. Tracking engine 105 also determines (406) the location of avatar 110 on map 130 relative to the location of virtual target 118 on map 130. Tracking engine 105 determines (408) whether the location of avatar 110 on map 130 matches the location of virtual target 118 on map 130.

In the illustrative example of FIG. 3, when tracking engine 105 determines that the location of avatar 110 on map 130 matches the location of virtual target 118 on map 130, tracking engine 105 generates (410) a message congratulating user 138 on locating virtual target 118. The message may include visual representation 116 displayed in graphical user interface 114, as illustrated in FIG. 1A. When tracking engine 105 determines that the location of avatar 110 on map 130 does not match the location of virtual target 118 on map 130, tracking engine 105 determines (412) whether the location of avatar 110 on map 130 indicates that avatar 110 has moved towards or away from virtual target 118, e.g., relative to a prior location of avatar 110 in map 130.

Using the determination of whether avatar 110 has moved towards or away from virtual target 118, application 104 generates (414) auditory stimulus 132. In an example, application 104 generates auditory stimulus 132 automatically and in real-time to promote an efficient and real-time auditory rehabilitation feedback loop. As previously described, auditory stimulus 132 may include numerous acoustic cues. The acoustic cues generated by diagnostic module 131 promote auditory rehabilitation in the areas of auditory perception that diagnostic module 131 identified as exhibiting auditory dysfunction.

In the illustrative example of FIG. 4, application 104 generates auditory stimulus 132 by using response information 134 to select an updated value from the range of values for an acoustic cue. As previously described, based on the types of auditory dysfunction, diagnostic module 131 determines a range of values for an acoustic cue. Within the range of values, application 104 may adjust the acoustic cues to train user 138 to perceive changes in properties of auditory stimulus 132 and thereby locate virtual target 118.

In an example, diagnostic module 131 determines that user 138 exhibits severe auditory dysfunction in the perception of soft sounds at a particular range of frequencies. To promote auditory rehabilitation in spectral perception, diagnostic module 131 determines that acoustic cues for spectral perception include tones ranging from 2000-8000 Hz, e.g., as illustrated in the above Table 1. In this example, tones ranging from 2000-8000 Hz are determined to be most effective in training individuals to detect properties of an audio signal that will enhance their perception of soft stimuli. Within the identified range of values, application 104 selects and/or determines a value for the acoustic cue based on the proximity of avatar 110 to virtual target 118. In this example, as avatar 110 moves towards virtual target 110, application 104 increases the decibel level of the acoustic cue towards the 60 dB value of the range. As avatar 110 moves away from virtual target 118, application 104 decreases the decibel level of the acoustic cue towards the 80 dB value of the range.

Computing device 102 plays (416) for user 138 auditory stimulus 132, e.g., via headphones 137. In response to hearing auditory stimulus 132, user 138 further moves avatar 110 in graphical user interface 106 in a direction that user 138 perceives as moving avatar 110 towards virtual target 118. Computing device 102 translates the movement of avatar 110 into response information 134 and the foregoing actions 404, 406, 408, 412, 414, 416 continue until user 138 locates virtual target 118 in graphical user interface 114. In this illustrative example of FIG. 4, application 104 implements an auditory rehabilitation feedback loop (e.g., a closed loop) through execution of actions 404, 406, 408, 412, 414.

Described herein is a system that promotes auditory rehabilitation in an individual with auditory dysfunction. The system is configured to diagnose auditory dysfunction in various types of auditory perception. Based on the type of diagnosed auditory dysfunction, the system is further configured to generate a rehabilitation program that promotes auditory rehabilitation by challenging the individual to locate a virtual target that is hidden in a virtual environment of the rehabilitation program.

To assist the individual in locating the virtual target, the rehabilitation program provides the individual with acoustic cues indicative of a proximity of an avatar in the virtual environment to the virtual target. In an example, the system generates an acoustic cue that promotes auditory rehabilitation for one or more of the types of diagnosed auditory dysfunction. By listening to, and learning from, the acoustic cues during play of the rehabilitation program, the system engages adaptive brain plasticity mechanisms of the individual (e.g., relative to the neural plasticity of the individual prior to playing the rehabilitation program). Based on the increase in neural plasticity, the individual may experience an improvement in hearing.

Embodiments can be implemented in digital electronic circuitry, or in computer hardware, firmware, software, or in combinations thereof. Apparatus of the invention can be implemented in a computer program product tangibly embodied or stored in a machine-readable storage device for execution by a programmable processor; and method actions can be performed by a programmable processor executing a program of instructions to perform functions of the invention by operating on input information and generating output. The invention can be implemented advantageously in one or more computer programs that are executable on a programmable system including at least one programmable processor coupled to receive information and instructions from, and to transmit information and instructions to, a information storage system, at least one input device, and at least one output device. Each computer program can be implemented in a high-level procedural or object oriented programming language, or in assembly or machine language if desired; and in any case, the language can be a compiled or interpreted language.

Suitable processors include, by way of example, both general and special purpose microprocessors. Generally, a processor will receive instructions and information from a read-only memory and/or a random access memory. Generally, a computer will include one or more mass storage devices for storing information files; such devices include magnetic disks, such as internal hard disks and removable disks; magneto-optical disks; and optical disks. Storage devices suitable for tangibly embodying computer program instructions and information include all forms of non-volatile memory, including by way of example semiconductor memory devices, such as EPROM, EEPROM, and flash memory devices; magnetic disks such as internal hard disks and removable disks; magneto-optical disks; and CD ROM disks. Any of the foregoing can be supplemented by, or incorporated in, ASICs (application-specific integrated circuits).

Other embodiments are within the scope and spirit of the description claims. For example, due to the nature of software, functions described above can be implemented using software, hardware, firmware, hardwiring, or combinations of any of these. Features implementing functions may also be physically located at various positions, including being distributed such that portions of functions are implemented at different physical locations.

What is claimed is:

1. A method performed by one or more processing devices, the method comprising:
   starting a program;
   generating data for a graphical user interface that when rendered on a display of a display device renders a visual representation of an object;
   identifying an auditory stimulus signal indicative of a location of a virtual target in the graphical user interface;
   receiving data representing a location of the visual representation of the object in the graphical user interface;
   intermittently determining whether a location of the visual representation of the object in the graphical user interface corresponds to the location of the virtual target until the location of the visual representation of the object in the graphical user interface corresponds to the location of the virtual target;
   while the location of the visual representation of the object in the graphical user interface does not correspond to the location of the virtual target,
      determining, based on processing of the data representing the location of the visual representation of the object, a proximity of the visual representation of the object to the virtual target in the graphical user interface;
      intermittently modifying, based on the proximity, the auditory stimulus signal by modifying a frequency of the auditory stimulus signal, a signal-to-noise ratio of the auditory stimulus signal, a sound level of the auditory stimulus signal, a binaural characteristic of the auditory stimulus signal, or a modulation of a sound envelope of the auditory stimulus signal; and
      causing one or more speaker devices to play the modified auditory stimulus signal;
   when the location of the visual representation of the object in the graphical user interface corresponds to the location of the virtual target,
      completing the program.

2. The method of claim 1, further comprising:
   detecting, following play of the auditory stimulus, that a location of the visual representation of the object in the graphical user interface corresponds to the location of the virtual target in the graphical user interface.

3. The method of claim 1, wherein the actions of receiving, determining, and intermittently modifying are repeated until a location of the visual representation of the object in the graphical user interface corresponds to the location of the virtual target in the graphical user interface.

4. The method of claim 1, further comprising:
   causing a diagnostic auditory signal to be played on the one or more speaker devices;
   receiving information indicative of a response of a user to the diagnostic auditory signal;
   determining, at least partly based on the received information, auditory dysfunction in one or more types of auditory perception of the user;
   determining, based on the determined auditory dysfunction, the frequency; and
   determining, based on one or more amounts of auditory dysfunction in the one or more types of auditory perception, one or more ranges of values for the frequency.

5. The method of claim 4, wherein the one or more ranges of values comprise one or more ranges of first values, and wherein the method further comprises:
   detecting a decrease in auditory dysfunction of the user; and
   updating, based on the detected decrease, the first values to second values, with the second values promoting an additional decrease in auditory dysfunction of the user.

6. The method of claim 1, further comprising:
   determining, based on the proximity, that the visual representation of the object has moved towards the virtual target; and
   generating a notification that the visual representation of the object has moved towards the virtual target.

7. The method of claim 1, further comprising:
   determining, based on the proximity, that the visual representation of the object has moved away from the virtual target; and
   generating a notification that the visual representation of the object has moved away from the virtual target.

8. The method of claim 1, wherein the auditory stimulus promotes auditory rehabilitation in a user by training the user to locate the virtual target in the graphical user interface based on a perception of the user of the frequency.

9. One or more machine-readable media configured to store instructions that are executable by one or more processing devices to perform operations comprising:
   starting a program;
   generating data for a graphical user interface that when rendered on a display of a display device renders a visual representation of an object;
   identifying an auditory stimulus signal indicative of a location of a virtual target in the graphical user interface;
   receiving data representing a location of the visual representation of the object in the graphical user interface;
   intermittently determining whether a location of the visual representation of the object in the graphical user interface corresponds to the location of the virtual target until the location of the visual representation of the object in the graphical user interface corresponds to the location of the virtual target;
   while the location of the visual representation of the object in the graphical user interface does not correspond to the location of the virtual target,
      determining, based on processing of the data representing the location of the visual representation of the object, a proximity of the visual representation of the object to the virtual target in the graphical user interface;
      intermittently modifying, based on the proximity, the auditory stimulus signal by modifying a frequency of the auditory stimulus signal, a signal-to-noise ratio of the auditory stimulus signal, a sound level of the auditory stimulus signal, a binaural characteristic of the auditory stimulus signal, or a modulation of a sound envelope of the auditory stimulus signal; and
      causing one or more speaker devices to play the modified auditory stimulus signal;
   when the location of the visual representation of the object in the graphical user interface corresponds to the location of the virtual target,
      completing the program.

10. The one or more machine-readable media of claim 9, wherein the operations further comprise:
   detecting, following play of the auditory stimulus, that a location of the visual representation of the object in the graphical user interface corresponds to the location of the virtual target in the graphical user interface.

11. The one or more machine-readable media of claim 9, wherein the actions of receiving, determining, and intermittently modifying are repeated until a location of the visual representation of the object in the graphical user interface corresponds to the location of the virtual target in the graphical user interface.

12. The one or more machine-readable media of claim 9, wherein the operations further comprise:
   causing a diagnostic auditory signal to be played on the one or more speaker devices;
   receiving information indicative of a response of a user to the diagnostic auditory signal;
   determining, at least partly based on the received information, auditory dysfunction in one or more types of auditory perception of the user;
   determining, based on the determined auditory dysfunction, the frequency; and
   determining, based on one or more amounts of auditory dysfunction in the one or more types of auditory perception, one or more ranges of values for the frequency.

13. The one or more machine-readable media of claim 12, wherein the one or more ranges of values comprise one or more ranges of first values, and wherein the operations further comprise:
   detecting a decrease in auditory dysfunction of the user; and
   updating, based on the detected decrease, the first values to second values, with the second values promoting an additional decrease in auditory dysfunction of the user.

14. The one or more machine-readable media of claim 9, wherein the operations further comprise:
   determining, based on the proximity, that the visual representation of the object has moved towards the virtual target; and
   generating a notification that the visual representation of the object has moved towards the virtual target.

15. The one or more machine-readable media of claim 9, wherein the operations further comprise:
   determining, based on the proximity, that the visual representation of the object has moved away from the virtual target; and
   generating a notification that the visual representation of the object has moved away from the virtual target.

16. The one or more machine-readable media of claim 9, wherein the auditory stimulus promotes auditory rehabilitation in a user by training the user to locate the virtual target in the graphical user interface based on a perception of the user of the frequency.

17. A system comprising:
   one or more processing devices; and
   one or more machine-readable media configured to store instructions that are executable by the one or more processing devices to perform operations comprising:
      starting a program;
      generating data for a graphical user interface that when rendered on a display of a display device renders a visual representation of an object;
      identifying an auditory stimulus signal indicative of a location of a virtual target in the graphical user interface;
      receiving data representing a location of the visual representation of the object in the graphical user interface;
      intermittently determining whether a location of the visual representation of the object in the graphical user interface corresponds to the location of the virtual target until the location of the visual representation of the object in the graphical user interface corresponds to the location of the virtual target;
      while the location of the visual representation of the object in the graphical user interface does not correspond to the location of the virtual target,
         determining, based on processing of the data representing the location of the visual representation of the object, a proximity of the visual representation of the object to the virtual target in the graphical user interface;

intermittently modifying, based on the proximity, the auditory stimulus signal by modifying a frequency of the auditory stimulus signal, a signal-to-noise ratio of the auditory stimulus signal, a sound level of the auditory stimulus signal, a binaural characteristic of the auditory stimulus signal, or a modulation of a sound envelope of the auditory stimulus signal; and causing one or more speaker devices to play the modified auditory stimulus signal;

when the location of the visual representation of the object in the graphical user interface corresponds to the location of the virtual target, completing the program.

18. The system of claim 17, wherein the operations further comprise:

detecting, following play of the auditory stimulus, that a location of the visual representation of the object in the graphical user interface corresponds to the location of the virtual target in the graphical user interface.

19. The system of claim 17, wherein the actions of receiving, determining, and intermittently modifying are repeated until a location of the visual representation of the object in the graphical user interface corresponds to the location of the virtual target in the graphical user interface.

20. The system of claim 17, wherein the operations further comprise:

causing a diagnostic auditory signal to be played on the one or more speaker devices;

receiving information indicative of a response of a user to the diagnostic auditory signal;

determining, at least partly based on the received information, auditory dysfunction in one or more types of auditory perception of the user;

determining, based on the determined auditory dysfunction, the frequency; and determining, based on one or more amounts of auditory dysfunction in the one or more types of auditory perception, one or more ranges of values for the frequency.

\* \* \* \* \*